United States Patent

Kuipers et al.

[11] Patent Number: 5,973,503
[45] Date of Patent: Oct. 26, 1999

[54] PROCESS AND MEASUREMENT SYSTEMS FOR MEASURING PHYSICAL QUANTITIES OF POORLY CONDUCTIVE AND NONCONDUCTIVE FLUIDS

[75] Inventors: Ulrich Kuipers, Olpe; Axel Barten, Siegen; Arnt Kohlrausch, Hilchenbach, all of Germany

[73] Assignee: Achenbach Buschhutten GmbH, Kreuztal, Germany

[21] Appl. No.: 08/890,977

[22] Filed: Jul. 10, 1997

[30] Foreign Application Priority Data

Jul. 17, 1996 [DE] Germany .................... 196 28 690

[51] Int. Cl.⁶ .................... G01N 27/08; G01R 27/08
[52] U.S. Cl. .................... 324/698; 324/439; 324/693; 324/724
[58] Field of Search .................... 324/439, 444, 324/445, 446, 448, 449, 450, 663, 664, 693, 694, 695, 696, 690, 722, 724, 704; 73/61.41, 61.43, 61.44, 61.61

[56] References Cited

U.S. PATENT DOCUMENTS

| | | | |
|---|---|---|---|
| 3,275,018 | 9/1966 | Roberts | 324/698 |
| 4,072,892 | 2/1978 | Lind | 324/448 |
| 5,396,178 | 3/1995 | Rybarski | 324/439 |
| 5,450,358 | 9/1995 | Seibert et al. | 324/694 |
| 5,521,510 | 5/1996 | Schunck | 324/439 |

FOREIGN PATENT DOCUMENTS

38 43 177  7/1990  Germany .

Primary Examiner—Diep N. Do
Attorney, Agent, or Firm—Young & Thompson

[57] ABSTRACT

A process for online measurement of electrical conductivity to control minimum conductivity of fluids, especially rolling oil, which prevents charging and discharging, by controlled addition of conductivity additives. The process measures the time change of conductivity to determine the amount of extremely fine particulate fouling and the degree of impurity of the rolling oil. The process also provides online measurement of the dielectric constant and online measurement of permeability.

16 Claims, 5 Drawing Sheets

PROCESS AND MEASUREMENT SYSTEMS FOR MEASURING PHYSICAL QUANTITIES OF POORLY CONDUCTIVE AND NONCONDUCTIVE FLUIDS

BACKGROUND OF THE INVENTION

The invention relates to a process and systems for measuring physical quantities of poorly conductive and nonconductive fluids such as rolling oil, lubricating oil, hydraulic fluid, brake fluids and fuels, the fluid being located between or in the field of action of at least two electrically conductive electrodes.

In the area of the rolling oil system of the primary tank of rolling units and in the area of roll stands deflagration and fires caused by electrostatic discharges occasionally occur.

Formation of electrostatic charges due to friction effects occurs in rolling oil in spite of grounding of the roll stands and all involved components when the electrical conductivity of the oil drops below a minimum value, so that balancing of electrical charges is no longer ensured.

To counteract the danger of electrostatic discharge processes and the associated danger of fire in rolling mills, the electrical conductivity of the rolling oil should be continuously checked. When the value drops below a certain threshold a conductivity additive can optionally be added to the oil.

Measuring devices are commercially available with which the electrical conductivity of fluids can be determined using different processes. Existing conductive measuring instruments for nonconductive or poorly conductive fluids such as oils or fuels are not suited for measurement in flowing media (online operation). The fluid to be measured must be at rest for several minutes in the known systems for the measuring instrument to display a reliable value. Running extraction of measurement samples is time-consuming and labor-intensive and is associated with the corresponding costs. Another disadvantage of offline measuring instruments is also that measured values of electrical conductivity of only limited reliability can be obtained since conductivity can be changed by many influences within a short time. When a value in the danger range is being measured efforts are made to reduce it again by adding additives, for example, to rolling oil, so that frictionless production can be ensured. Since the time intervals between sampling and the measuring instant are considerable due to the rest time of the oil prescribed by the measuring instrument manufacturer, under certain circumstances it can already be too late to eliminate the danger of electrostatic discharges.

This applies especially to a mechanical filtering process in which the abraded rolled material is filtered out of the rolling oil and large amounts of electrical charge are produced by charge separation or frictional electricity due to division and branching of the oil flow via the pores and fine capillaries of a filtering agent such as kieselguhr.

One major disadvantage of commercially available measuring instruments for measuring electrical conductivity of poorly conductive or nonconductive fluids is that the inevitable parasitic capacitances of the sensors used in the measuring instruments, like polarization capacitances, cause major measurement deviations.

To measure the fouling of fluids optical measuring devices are commercially available with which the cloudiness is measured to determine the degree of fouling of the fluids. But in the meantime it has been ascertained that cloudiness is not a measure of the degree of fouling of many fluids, for example, oils, since the geometrical dimensions of the dirt particles contained in the fluid are to some extent smaller than the wavelength of the light, so that these extremely small dirt particles are no longer recorded by measurement of cloudiness based on light refraction.

The faulty manner of operation of commercially available devices for measurement of electrical conductivity and the degree of fouling of oils, fuels and similar nonconductive and poorly conductive fluids leads to agents for increasing the electrical conductivity of fluids such as rolling oil being added to them preventatively and filtering agents such as kieselguhr and bleaching earth being replaced long before or shortly after their exhaustion when oils are being filtered. Known agents which are also called conductivity additives for increasing conductivity are suspect both ecologically and in terms of health so that wholesale preventative addition of these agents causes high environmental burdens and disposal problems. High filtrate quality caused by increased use of filtering agents and reactions of the conductivity additive with filtering aids can greatly reduce the conductivity of oil and oil products, and due to reduced conductivity high electrical charges occur which can lead to uncontrolled deflagration and burning of machinery and plants.

SUMMARY OF THE INVENTION

The object of the invention is to develop a process designed for poorly conductive and nonconductive fluids such as rolling oil, lubricating oil, hydraulic fluid, brake fluids and fuels and measurement systems using the process for online measurement of electrical conductivity to control minimum conductivity which prevents charging and discharging by controlled introduction of conductivity additives, online measurement of the time change of conductivity for determining amounts of extremely fine particulate fouling and the degree of impurity, difference measurement of the conductivity in front of and behind a filter for testing operation and quality of a filtering process and optionally for control of the filtering process by controlled supply of filtering aids, for online measurement of the dielectric constant for acquiring polar components such as oil additives or water, and for online measurement of permeability for determining the concentrations of iron particles or ferromagnetic abrasion particles.

BRIEF DESCRIPTION OF THE DRAWINGS

The measurement systems according to the invention for measuring different physical quantities of poorly conductive and nonconductive fluids such as rolling oil and the advantages of the measurement systems over prior art are explained below using schematic drawings which in particular show the following.

DESCRIPTION OF THE PREFERRED EMBODIMENTS

Figure 1:
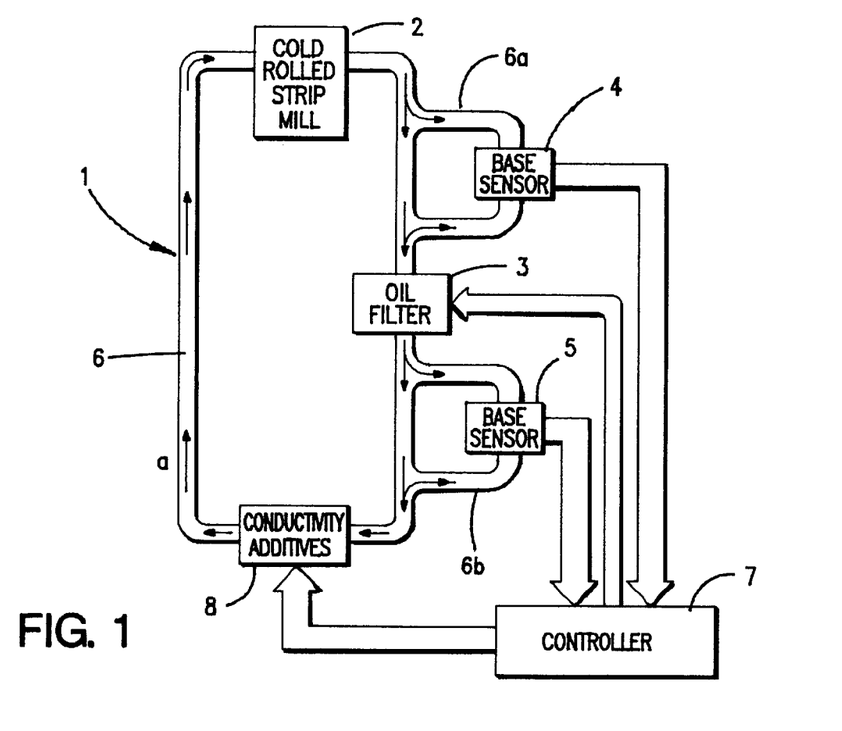
FIG. 1 shows a schematic of a rolling oil circuit with a measurement system for determining the conductivity of rolling oil.

Rolling oil circuit 1 shown schematically in FIG. 1 for cold rolled strip mill 2 with lubrication and cooling oil for the rolling process is equipped with a measurement system for online measurement of electrical conductivity of the rolling oil, of the degree of oil fouling which is caused mainly by the abrasion of the rolls and rolled articles as well as additives, and the quality of the filtering process of oil filter 3 located in the circuit.

The measurement system comprises two identical base sensors 4, 5. Base sensor 4, viewed in peripheral direction a of the rolling oil, is installed in bypass line 6a of main line 6 of rolling oil circuit 1 in front of oil filter 3 and base sensor 5 in bypass line 6b of main line 6 behind oil filter 3.

With base sensor 5 installed behind oil filter 3 in bypass line 6b the absolute value of the electrical conductivity of the rolling oil is continuously measured to determine the degree of electrostatic charging with respect to preventing electrostatic discharges. The measurement signals of base sensor 5 are transmitted to control means 7 which controls device 8 for adding conductivity additives to rolling oil circuit 1. By adding conductivity additives the required minimum conductivity of the rolling oil of 50 pS/m is maintained.

The absolute value of electrical conductivity of the rolling oil which must be optionally referenced to the oil temperature and which is measured by base sensor 5 behind oil filter 3 is furthermore a criterion for the degree of fouling of the oil and thus decisive for the time of processing of the used rolling oil which can no longer by cleaned by a filtering process, using a distillation or rectification process.

By means of the difference values which result from the values of electrical conductivity of the rolling oil measured by base sensor 4 in front of oil filter 3 and the conductivity values measured by base sensor 5 behind oil filter 3, the quality of the filtering process is evaluated and the time of required cleaning of the filter or renewal of the filtering agent is ascertained and the supply of filtering aids is controlled.

Figure 2:
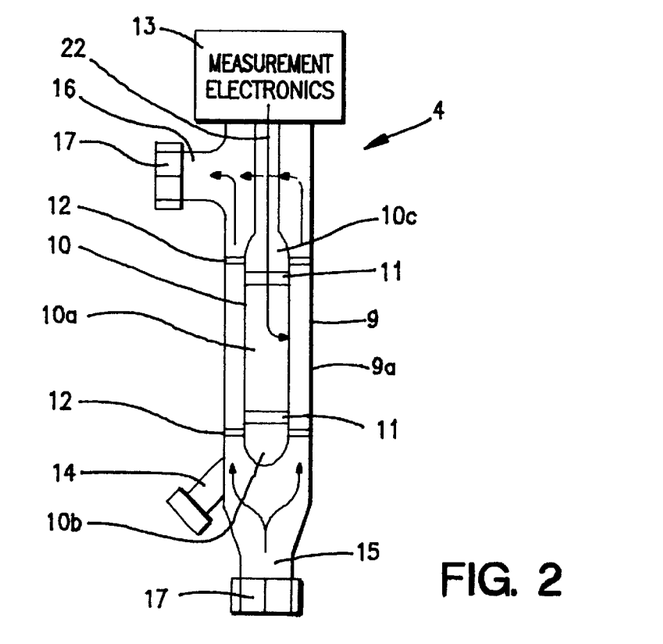
FIG. 2 shows a schematic longitudinal section of a base sensor.

Base sensor 4 according to FIG. 2 which can be used to measure the electrical conductivity κ, dielectric constant εr, permeability $\mu$ and viscosity η of poorly conductive and nonconductive fluids such as rolling oil is installed in the vertical position in bypass line 6a of main line 6 of rolling oil circuit 1 to prevent the air in the oil circuit from collecting in the base sensor which would adulterate the measurement results. Base sensor 4 has outer electrode 9 which is made as electrically conductive metallic tube segment 9a in which there is electrically conductive inner electrode 10 which is preferably made in the shape of a flow line and around which fluid flows. Cylindrical inner electrode 10 is divided into middle useful electrode 10a and one front and one rear shielding electrode 10b, 10c. Useful electrode 10a of inner electrode 10 is separated by insulation 11 from two shielding electrodes 10b, 10c. Inner electrode 10 is held by two spacers 12 in base sensor 4, spacers 12 being installed between outer electrode 9 and two shielding electrodes 10b, 10c. This arrangement prevents nonhomogeneous edge fields which lead to false measurement results when electrically conductive dirt particles are deposited on spacers 12. Inner electrode 10 is made partially as a hollow body for the bushing of power leads for measurement electronics 13.

Temperature sensor 14 which is installed in outer electrode 9 of base sensor 4 is used to measure the temperature of the rolling oil.

To measure the viscosity of the rolling oil, inner electrode 10 of base sensor 4 can be equipped with a rotary drive with power consumption or rpm which constitutes a measurement quantity for the viscosity of the rolling oil.

Tubular outer electrode 9 has one inlet and one outlet connector 15, 16, each with tube connection 17 for installation of base sensor 4 in bypass line 6a of main line 6 of rolling oil circuit 1.

To determine electrical conductivity K of the rolling oil ohmic resistance $R_x$ of the oil between outer electrode 9 and inner electrode 10 of base sensor 4 is measured with the measurement system described below.

Figure 3:
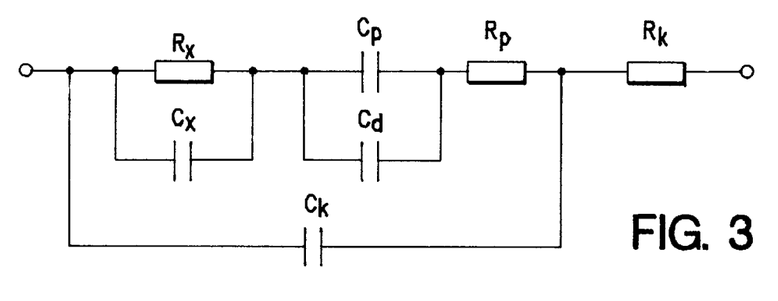
FIG. 3 shows the equivalent circuit diagram of the base sensor according to FIG. 2, taken from: Oehme, F.: Chemical Sensors, Vieweg 1991.

The equivalent circuit diagram of the overall sensor according to FIG. 3 shows that unknown resistance $R_x$ is an element of a network of parasitic resistors and capacitors. In the equivalent circuit diagram $R_x$ is the unknown resistance $C_x$ is the sensor capacitance $R_p$ is the polarization resistance $C_p$ is the polarization capacitance $C_d$ is a double layer capacitance $C_k$ is the cable capacitance $R_k$ is the cable and contact resistance This equivalent circuit diagram can be greatly simplified using an appropriate sensor signal when the sensor layout is suitable. Thus $C_k$ and $R_k$ can be ignored if the connections to the inner or outer electrodes are laid separately, the connection of the inner electrode is made via coaxial cable, and the outer conductor of the coaxial cable is suitably connected.

Figure 4:
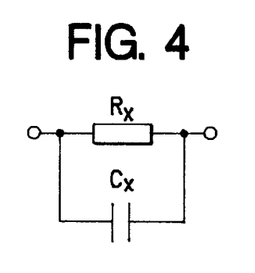
FIG. 4 shows the simplified equivalent circuit diagram of the base sensor.

The conductivity decreases when a dc voltage is applied. This can be attributed to the formation of $C_p$, $C_d$, and $R_p$. If a measurement signal with changing polarity is used, these components can also be ignored in the equivalent circuit diagram. This yields the final equivalent circuit diagram of the base sensor according to FIG. 4.

Figure 5:
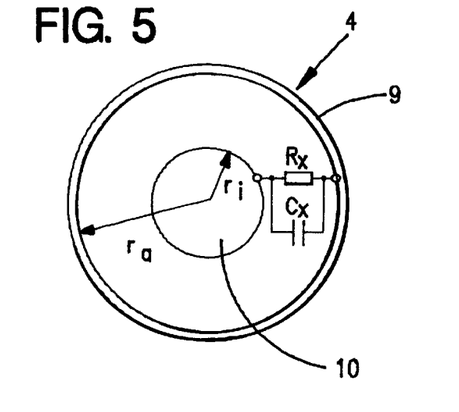
FIG. 5 shows a schematic cross section of the base sensor according to FIG. 2.
Figure 6:
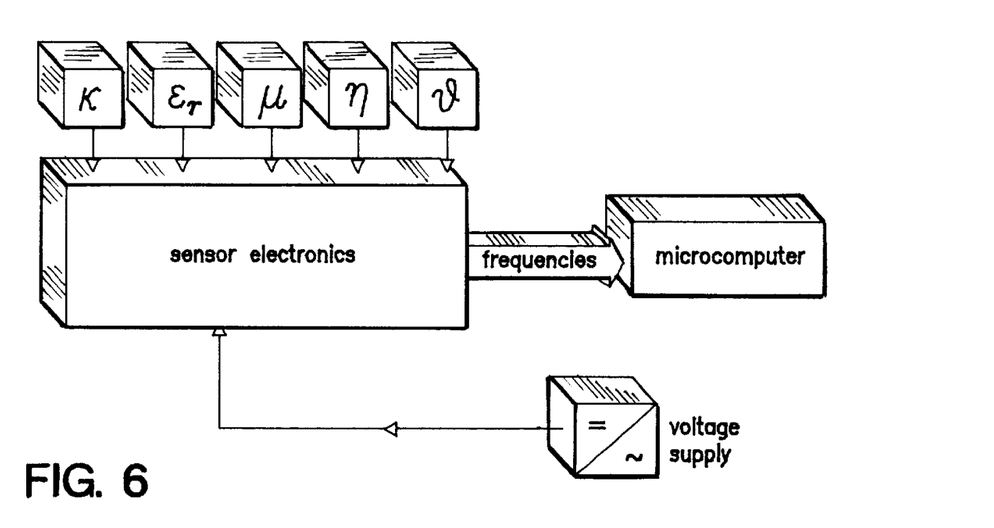
FIG. 6 shows the block diagram of a measurement system with the base sensor according to FIGS. 2 through 5 for measuring different physical quantities of poorly conductive and nonconductive fluids.

Using the basic formulas for homogeneous flow fields, at a given sensor geometry resistance $R_x$ and specific conductivity κ of sensor 4 shown in FIG. 5 in cross section can be computed with a coaxial arrangement of outer electrode 9 and inner electrode 10 in the form of a single layer cylinder capacitor as follows $$R_x = [ln(r_a/r_i)]/(2\pi l k) \quad (1)$$

where $r_a$ is the inside radius of the outer electrode $r_i$ is radius of the inner electrode l is the active electrode length FIG. 6 shows the block diagram of the new measurement system with the above described base sensor for measuring the specific conductivity κ, dielectric constant ∈r, ferromagnetic permeability μ, viscosity η, and temperature ν of poorly conductive and nonconductive fluids such as rolling oil.

The measurement system claimed in the invention with the pertinent electronics for determining unknown resistance $R_x$ and parasitic sensor capacitance $C_x$ is explained below. If resistance $R_x$ and sensor capacitance $C_x$ are known, the specific conductivity κ and dielectric constant $\epsilon_r$ can be computed. Since these two quantities are dependent on temperature, a temperature measurement which is not detailed is necessary.

Integrating measurement systems are used to determine resistance $R_x$ and parasitic sensor capacitance $C_x$. These measurement systems are characterized by high noise suppression and offer the further advantages that the measured quantities obtained using integration can be easily converted into frequencies which can be measured very accurately. Other advantageous properties of frequencies are noiseless long-distance transmission of the measurement signal and simple digitization. This is of decisive importance since quantities $R_x$ and $C_x$ to be determined are recorded with a microcomputer as follows from the block diagram of the measurement system according to FIG. 6. In this measurement system the voltage supply is located separately to preclude adverse effects on the measurement electronics caused thereby.

The equivalent circuit diagram of the conductivity sensor is reduced to the parallel connection of resistance $R_x$ and capacitance $C_x$. To determine conductivity however only resistance $R_x$ is relevant, i.e., parasitic sensor capacitance $C_x$ should not be included in the measurement result. One possibility for eliminating the capacitance is to measure with a dc voltage. For the charged capacitor then the following applies according to $$i_c = C \times [du(t)/dt] \text{ with } du/dt=0 : i_c=0 \quad (2)$$

Figure 7:
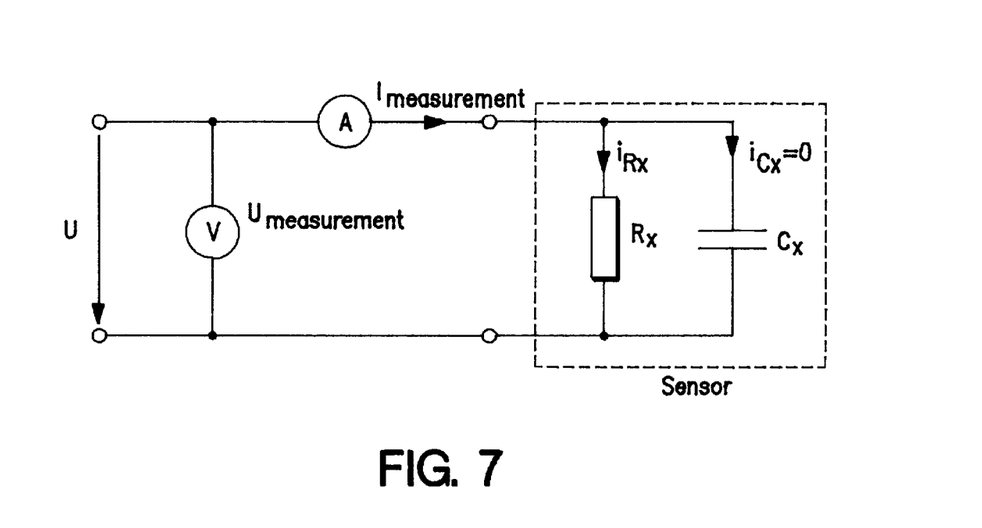
FIG. 7 shows the circuit diagram of a base sensor operated with a dc voltage for measuring the ohmic resistance of a fluid.

The measurement system as shown in FIG. 7 does compensate for sensor capacitance $C_x$, but at the same time other disturbances can take effect. Primarily polarization makes it impossible to determine resistance via a dc voltage measurement. In addition, offset quantities of the operational amplifier would cause further adulteration of the measurement result. To prevent this it is essential to work with an ac voltage. Since however a pure sinusoidal voltage does not compensate for the reactive current of the sensor capacitance, it is measured at the same time. The process claimed in the invention works with a bipolarly clocked dc voltage, however measurements being taken only in the time intervals in which the voltage on the sensor is constant.

Figure 8:
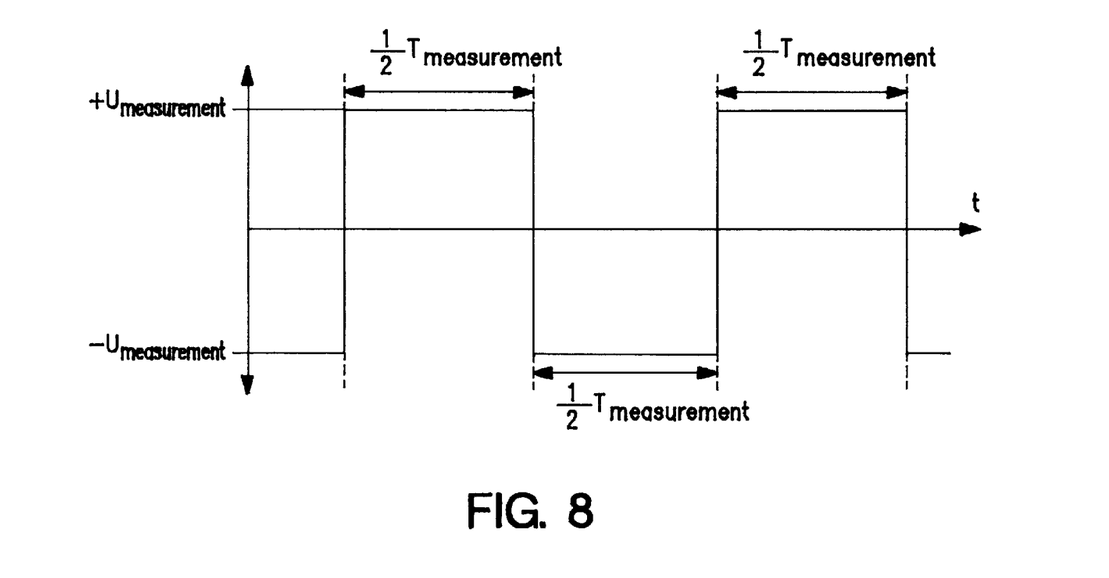
FIG. 8 shows the behavior of a bipolarly clocked dc voltage for operating a base sensor for measuring the ohmic resistance of a fluid.

FIG. 8 shows the behavior of the bipolarly clocked dc voltage with the measurement intervals drawn in.

Figure 9:
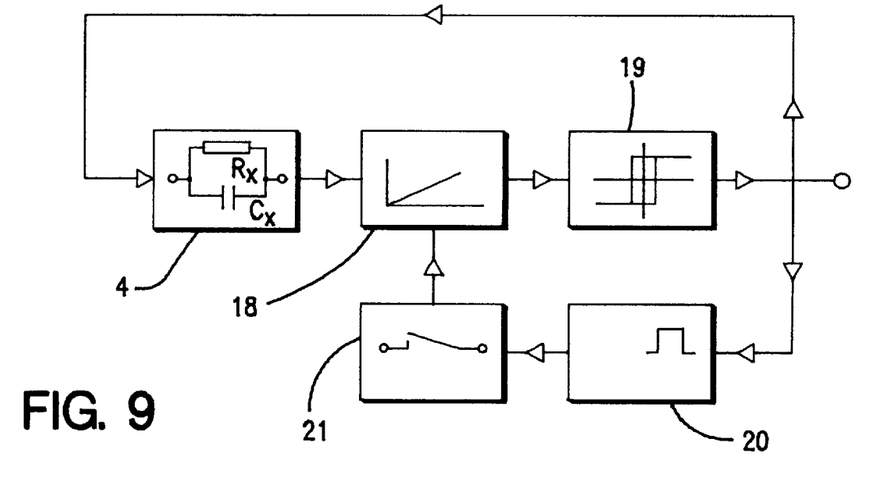
FIG. 9 shows the block diagram of a measurement system for measuring the electrical conductivity of a fluid.

In the measurement system for measuring the specific electrical conductivity of a poorly conductive or nonconductive fluid such as rolling oil which is shown in the simplified block diagram in FIG. 9, a test signal in the form of a clocked dc voltage with frequency which is dependent on the value of conductivity K is switched to base sensor 4. The output voltage of base sensor 4 is integrated by integrator 18 and the output signal of integrator 18 is switched to Schmitt trigger 19 with its output signal in turn switched to base sensor 4 as the test signal. Integration is set to zero for each change of the test signal.

The switching concept for the measurement system for measuring conductivity consists essentially of an astable flip-flop with reversing integrator 18 and noninverting Schmitt trigger 19, switch 21 controlled by monoflop 20 deactivating integrator 18 during the change of polarity of the measurement voltage and zeroing it to the initial condition.

The integrator used in the measurement system with the operational amplifier and integration capacitor $C_n$ is decisive for measurement accuracy. Since resistance $R_x$ to be measured can assume values into the teraohm range for very low conductivities of a fluid, the operational amplifier used should have a high input resistance. The offset quantities are eliminated by the measurement process as claimed in the invention.

Figure 10:
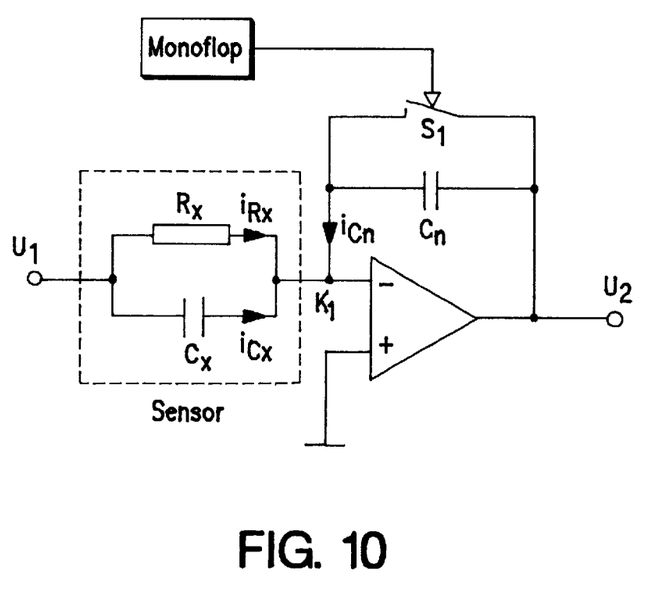
FIG. 10 shows the circuit diagram of the integrator used according to FIG. 9 with sensor and analog switch.
Figure 11:
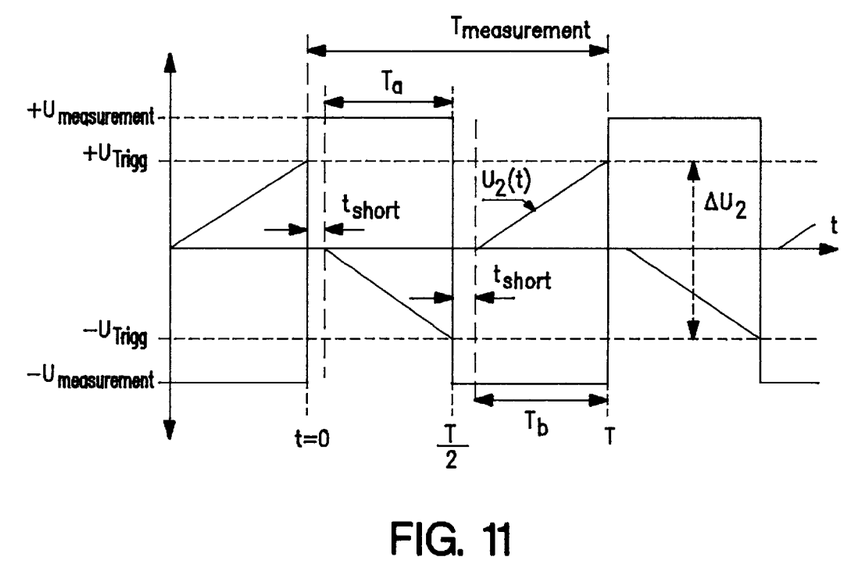
FIG. 11 shows the diagram of the clocked input voltage and the output voltage of the integrator and FIG. 12 shows the block diagram of a measurement system for measuring the electrical conductivity and the dielectric constant of a fluid.

FIG. 10 shows the active integrator with its wiring. The sensor consisting of the parallel connection of $R_x$ and $C_x$ forms the input impedance. Integration capacitor $C_n$ is in feedback and parallel to it is analog switch $S_1$ controlled via a monoflop.

If clocked dc voltage $U_1$ changes its sign, switch $S_1$ is closed. Since the integrator is then in direct negative feedback, output voltage $U_2$ jumps to zero volts at this time and integration capacitor $C_n$ is discharged via switch $S_1$. Parasitic sensor capacitance $C_x$ is simply recharged during the change of polarity of $U_1$.

If the measurement voltage again reaches a constant value, $S_1$ opens and the integration process is started. Since $C_x$ is now charged and thus according to equation (2) $i_c=0$, only measurement current $i_{Rx}$ flowing via unknown resistance $R_x$ is integrated.

The output frequency of the electronics is $$f = \frac{\pi \cdot l \cdot R_3}{R_2 \cdot C_n \cdot \ln\left(\frac{r_a}{r_i}\right)} \cdot \kappa \quad (6)$$

The frequency according to equation (3) is a linear function of κ. The other quantities are constant. They are based on the geometrical dimension of the sensor and on the resistance ratio $R_3/R_2$ which determines the operating points of the Schmitt trigger which is not detailed.

Computation of the integrator according to FIG. 10 shows that with short circuiting of the integration capacitor during the change of polarity of $U_{meas}$ the parasitic sensor capacitance can be eliminated, To do this switch $S_1$ must be triggered with a control pulse of constant length $t_{short}$.

Analogously to the measurement system explained using FIG. 9 for measuring the specific electrical conductivity of a poorly conductive or nonconductive fluid such as rolling oil, in a measurement system for online measurement of the dielectric constant $\epsilon_r$ of this fluid a test signal in the form of a clocked dc voltage with a frequency which is proportional to the value of dielectric constant $\epsilon_r$ is switched to a base sensor. The developing output voltage of the integrator implemented in this way is switched to a Schmitt trigger with its output signal converted into a current in turn switched to the base sensor as the test signal.

Figure 12:
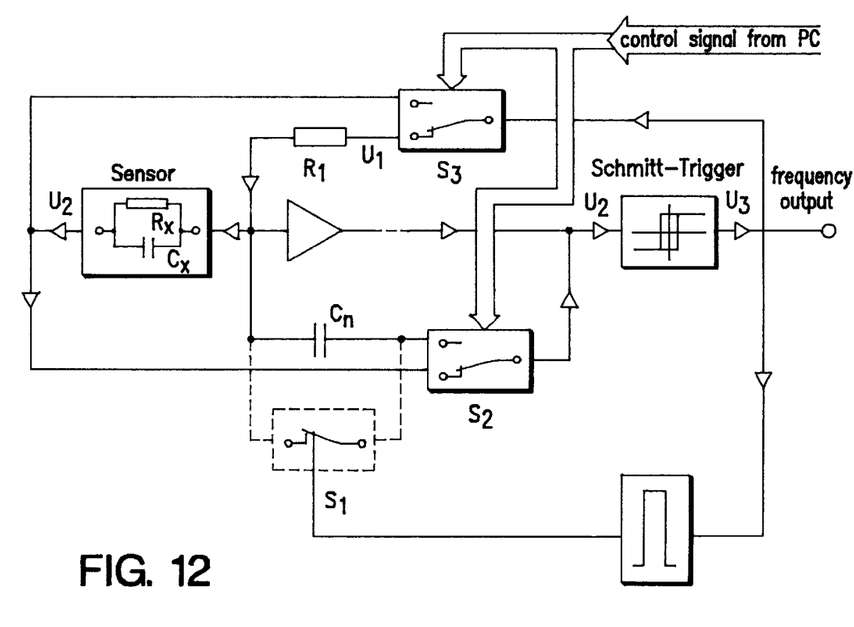

FIG. 12 illustrates the block diagram of a measurement system for measuring the conductive and dielectric constant of a fluid.

Analogously to the above described measurement systems for measuring the conductive and dielectric constant of fluids, in a measurement system for online measurement of permeability μ of poorly conductive and nonconductive fluids a test signal in the form of a clocked dc voltage with a frequency which is a function of permeability $\mu$ is switched to a base sensor. The developing current is converted into a voltage by the base sensor and the output voltage of the integrator implemented in this way with the sensor inductance switched into the inverting input branch of an operational amplifier looped back via an ohmic resistance is switched to a Schmitt trigger with an output voltage which in turn is switched to the base sensor as the test signal.

By measuring the dielectric constant the water content can be determined for example in transformer oils, brake fluids and aviation gasoline. Brake fluid can absorb water which forms vapor bubbles in it which adversely affect the serviceability of the braking system in motor vehicles. In aircraft exposed to temperatures down to −40° C., water contained in the brake fluid can form ice crystals which clog lines and valves of the braking system and thus reduce braking performance so that when aircraft land the danger of accident can arise. Water in aviation gasoline can also reduce the power of aircraft engines for example by icing or bubble formation. At the same time measurement of the dielectric constant of aviation gasoline becomes important for safety in the fueling of aircraft and during running measurement of the dielectric constant of the brake fluid of the braking system of aircraft for determining the water content of the aviation gasoline or the brake fluid.

By means of running measurement of the permeability of the lubricating oil of for example engines, transmissions, and power plant turbines, abraded ferromagnetic particles which originate for example from turbine bearings and which are contained in the oil can be detected so that early recognition of incipient bearing damage is possible and turbine damage which leads to longer downtimes of sections of a power plant can be prevented by early replacement of bearings.

The above description shows that the measurement process claimed in the invention and the corresponding measurement systems for measuring conductivity, dielectric constant and permeability of poorly conductive and nonconductive fluids such as rolling oil, lubricating oils, brake fluids and aircraft fuel will acquire great importance in many technical applications in the future.

We claim:

1. A process for continuous measurement of a physical characteristic of a fluid that is poorly conductive or nonconductive and that is moving between two electrically conductive electrodes of a sensor, the process comprising the steps of:

applying a signal across the two electrodes of the sensor to continuously measure an electrical conductivity $\kappa$ of the poorly conductive or nonconductive fluid as it moves between the two electrodes, the signal being a clocked direct voltage or current;

integrating an output from the sensor with an integrator and applying the integrated output to a Schmitt trigger whose output is the clocked signal that is applied across the two electrodes, wherein a frequency of the clocked signal is a function of the electrical conductivity $\kappa$; and resetting the integrator to zero with each clocked transition of the signal.

2. The process of claim 1, further comprising the step of determining that a danger of electrostatic charges or discharges exists when the measured electrical conductivity $\kappa$ falls below a predetermined value.

3. The process of claim 2, further comprising the step of-adding an anti-static additive to the fluid when the measured electrical conductivity $\kappa$ falls below the predetermined value.

4. The process of claim 1, further comprising the steps of filtering the moving fluid with a filter, measuring the electrical conductivity $\kappa$ upstream and downstream of the filter, determining a difference between the upstream and the downstream measured conductivity $\kappa$, and changing the filtering based on the determined difference.

5. The process of claim 1, further comprising the step of initiating an automatic self-calibration.

6. The process of claim 1, wherein the fluid is one of oil, brake fluid, and fuel.

7. A process for continuous measurement of a physical characteristic of a fluid that is poorly conductive or nonconductive and that is moving between two electrically conductive electrodes of a sensor, the process comprising the steps of:

applying a signal across the two electrodes of the sensor to continuously measure a dielectric constant $\epsilon_r$ of the poorly conductive or nonconductive fluid as it moves between the two electrodes, the signal being a clocked direct current;

integrating an output from the sensor with an integrator and applying the integrated output voltage to a Schmitt trigger whose output is converted to a current and is the clocked signal that is applied across the two electrodes, wherein a frequency of the clocked signal is a function of the dielectric constant $\epsilon_r$; and resetting the integrator to zero with each clocked transition of the signal.

8. The process of claim 7, further comprising the step of initiating an automatic self-calibration.

9. The process of claim 7, wherein the fluid is one of oil, brake fluid, and fuel.

10. A process for continuous measurement of a physical characteristic of a fluid that is poorly conductive or nonconductive and that is moving between two electrically conductive electrodes of a sensor, the process comprising the steps of:

applying a signal across the two electrodes of the sensor to continuously measure a permeability $\mu$ of the poorly conductive or nonconductive fluid as it moves between the two electrodes, the signal being a clocked direct voltage;

integrating an output from the sensor with an integrator and applying the integrated output to a Schmitt trigger whose output is the clocked signal that is applied across the two electrodes, wherein a frequency of the clocked signal is a function of the permeability $\mu$; and resetting the integrator to zero with each clocked transition of the signal.

11. The process of claim 10, further comprising the step of initiating an automatic self-calibration.

12. The process of claim 10, wherein the fluid is one of oil, brake fluid, and fuel.

13. A device for continuous measurement of a physical characteristic of a moving fluid that is poorly conductive or nonconductive, the device comprising:

a sensor comprising an inner electrically conductive electrode within a cylindrical outer electrically conductive electrode, an annular space between said inner and outer electrodes defining a passage for the fluid, said inner electrode comprising an electrically conductive hollow active electrode and electrically conductive hollow shield electrodes which are electrically isolated from said active electrode;

retainers contacting said shield electrodes and an interior of said outer electrode for holding said inner electrode within said outer electrode;

means for applying the same but independent clocked direct voltages to said active electrode and said shield electrodes;

means for determining a resistance $R_x$ between said inner and outer electrodes and for generating a frequency change of the clocked direct voltages based on the determined resistance; and means for continuously measuring the physical characteristic of the fluid based on the measured resistance between said inner and outer electrodes.

14. The device of claim 13, wherein said inner electrode is rotatable.

15. The device of claim 13, further comprising an integrator for integrating an output from said sensor, a Schmitt trigger for receiving an integrated output from said integrator, and means for feeding back the output from said Schmitt trigger to said sensor as a clocked feedback voltage.

16. The device of claim 13, wherein said outer, inner, and shield electrodes are coaxial.

* * * * *